United States Patent
Miller

(10) Patent No.: US 8,459,178 B2
(45) Date of Patent: Jun. 11, 2013

(54) TEA BREWING AND DISPENSING SYSTEM AND METHOD

(76) Inventor: Harold F Miller, Summerville, SC (US)

( * ) Notice: Subject to any disclaimer, the term of this patent is extended or adjusted under 35 U.S.C. 154(b) by 693 days.

(21) Appl. No.: 12/654,400

(22) Filed: Dec. 18, 2009

(65) Prior Publication Data

US 2010/0173048 A1 Jul. 8, 2010

Related U.S. Application Data

(60) Provisional application No. 61/203,284, filed on Dec. 19, 2008.

(51) Int. Cl.
*A47J 31/00* (2006.01)

(52) U.S. Cl.
USPC ............................................. 99/289 R

(58) Field of Classification Search
USPC ................................................. 99/289 R, 279
See application file for complete search history.

(56) References Cited

U.S. PATENT DOCUMENTS

| | | | |
|---|---|---|---|
| 4,919,041 A | 4/1990 | Miller | |
| 4,967,648 A * | 11/1990 | Helbling | 99/280 |
| 5,116,632 A | 5/1992 | Miller | |
| 5,192,571 A | 3/1993 | Levy | |
| 5,733,591 A | 3/1998 | Goerndt | |
| 6,095,031 A | 8/2000 | Warne | |
| 6,120,825 A | 9/2000 | Cirigliano et al. | |
| 6,571,685 B1 | 6/2003 | Lassota | |
| 6,915,926 B2 | 7/2005 | Naik | |
| 6,962,104 B1 * | 11/2005 | Podlucky et al. | 99/300 |
| 6,981,441 B1 | 1/2006 | Dussinger | |
| 6,988,641 B2 | 1/2006 | Jones et al. | |
| 7,067,168 B1 | 6/2006 | Podlucky et al. | |
| 7,631,593 B2 | 12/2009 | Lassota et al. | |

FOREIGN PATENT DOCUMENTS

JP 2001057846 A * 3/2001

* cited by examiner

*Primary Examiner* — Gene Kim
*Assistant Examiner* — Amir Klayman
(74) *Attorney, Agent, or Firm* — Joan K. Lawrence, Esq.

(57) ABSTRACT

An automatically controllable commercial system for brewing a consistently high quality cold brewed beverage from a supply of purified water, optionally sweetening the brewed beverage, and dispensing the cold brewed beverage is provided. The system of the present invention includes automatically controllable integrated components for purifying the water supplied to brew the beverage and for maintaining the system in a sanitary condition that can be serviced on site or from a remote location. The present invention further provides an automated, commercial scale method for brewing tea from real tea leaves and naturally sweetening the tea to produce cold sweet tea with the high quality taste of homemade sweet tea.

18 Claims, 3 Drawing Sheets

TEA BREWING AND DISPENSING SYSTEM AND METHOD

The present invention claims priority from U.S. Provisional Patent Application Ser. No. 61/203,284, filed Dec. 19, 2008, the disclosure of which is incorporated herein by reference.

TECHNICAL FIELD

The present invention relates generally to automatic commercial brewing and dispensing systems for brewed beverages and specifically to an improved commercial brewing and dispensing system and method that automatically and safely produces a consistently reliable supply of high quality tea brewed from tea leaves and naturally sweetened to produce a sweet tea beverage with a superior taste.

BACKGROUND OF THE INVENTION

Tea is a beverage that has become increasingly popular with consumers in recent years. It is viewed by many as a healthier beverage choice than a soft drink. After water, tea is the most popular beverage in the world. An estimated 85% of the tea imported into the United States in served over ice. Consequently, fast food outlets and other kinds of restaurants have increased their tea offerings to keep up with consumer demand. Iced tea and sweetened iced tea, especially in the South, are often requested instead of the ubiquitous carbonated sodas. Producing, on a commercial scale from real tea leaves, a high quality iced tea and sweetened iced tea that consistently tastes like it was brewed at home, but can be dispensed like soft drinks, presents challenges. Currently available commercial systems and methods for supplying iced tea have not produced a consistently high quality iced or sweetened iced tea beverage.

The prior art describes many variations on the brewing and dispensing of tea, iced and hot, as well as sweetened and unsweetened. U.S. Pat. No. 7,067,168 to Podlucky et al, for example, describes an automated tea brewing system that can produce sweetened or unsweetened tea. This system produces a tea concentrate that can then be sweetened with a liquid sweetener and diluted to generate very large quantities of tea for bottling. U.S. Pat. No. 6,981,441 to Dussinger and U.S. Pat. No. 6,988,641 to Jones et al both describe iced tea brewing systems that use a tea concentrate. Dussinger brews the concentrate and adds chilled water, while the Jones et al tea product is a post mix designed to have the appearance of fresh brewed tea. None of these systems produces a tea product that has the taste of fresh brewed tea, however.

The maintenance of a commercial brewed beverage system in a sanitary condition that avoids the growth of microorganisms is an additional challenge, especially when the brewed beverage system provides for the addition of sweetener to the beverage. Preventing the growth of potentially harmful microorganisms in the components of a commercial beverage brewing system is critical. Goerndt, in U.S. Pat. No. 5,733,591, describes a method for automatically sweetening tea that employs a timed control circuit to produce a sweetened or unsweetened tea beverage. A viscous corn sweetener is added to hot tea to form a concentrate that is then diluted. Although Goerndt also describes purging the system lines as tea canisters are prepared, this is appears to be done with tea or water, which is does not guarantee thorough sanitization of this system. In U.S. Pat. No. 6,915,926, Naik discloses automatically cleaning a cold beverage dispensing system using hot water. While this method may clean the premix powder and water system described by Naik, it is of limited value in disinfecting tea brewing system components that use fresh tea leaves or liquid sweetener. Cirigliano et al additionally recognize the need for sanitizing a tea brewing system to eliminate or substantially reduce microbial growth in U.S. Pat. No. 6,120,825. Their sanitization method also employs hot water, however. The use of ozone to disinfect and sanitize a tea brewing and dispensing system that uses fresh tea leaves or a liquid sweetener does not appear to have been contemplated by the prior art.

An additional challenge encountered in the production of an iced tea or sweetened iced tea beverage on a commercial scale that tastes good may arise from the quality of the available water supply. The chlorine and chloramines used in the treatment of most local water supplies, for example, can adversely affect the taste of brewed beverages and may give tea a bad taste. In U.S. Pat. No. 5,192,571, Levy recognizes this challenge, and addresses it by adding anhydrous thiosulfates to tea and other beverages. This may eliminate the taste of chlorine or chloramine, but may also adversely affect the taste of the brewed tea.

Control systems for automatic beverage brewing systems are described in the art. U.S. Pat. No. 6,095,031 to Warne, U.S. Pat. No. 6,571,685 to Lassota, and U.S. Pat. No. 7,076,966 to Lassota et al, for example, all describe such control systems. The Warne system focuses on a control system based on temperature detection parameters, the Lassota et al system discloses switches that interact with a manual control system, and Lassota employs a specific microprocessor to drain the disclosed system so that the tea can be contacted with atmospheric oxygen during the brewing cycle.

The prior art, therefore, fails to provide an automatically controllable system for brewing and dispensing cold unsweetened tea or sweetened tea characterized by a consistently high quality superior taste on a commercial scale with the advantages of the present invention.

SUMMARY OF THE INVENTION

It is a primary object of the present invention to overcome the disadvantages of the prior art and to provide an improved commercial cold or iced beverage brewing and dispensing system useful in a range of different types of restaurants that automatically and consistently produces a cold or iced beverage with a superior taste.

It is another object of the present invention to produce an improved commercial brewing and dispensing system that automatically brews tea from tea leaves and adds a natural sweetener to produce sweet tea with a superior taste.

It is a further object of the present invention to provide a fully automated commercial tea brewing and dispensing system and method that consistently produces a naturally sweetened cold tea with a taste that approximates the taste of home brewed sweet tea.

It is yet another object of the present invention to provide a fully automated commercial cold beverage brewing and dispensing system including an integrated component for purifying the water used to prepare the brewed beverage.

It is yet a further object of the present invention to provide a fully automated commercial cold beverage brewing and dispensing system including an integrated component for automatically sanitizing the brewing, sweetening, and dispensing components of the system.

It is a still further object of the present invention to provide an automatically controllable commercial cold beverage brewing and dispensing system that can be monitored and adjusted from a remote location.

In accordance with the aforesaid objects, an automatically controllable commercial system for brewing a consistently high quality cold brewed beverage from a supply of purified water, optionally sweetening the brewed beverage, and dispensing the cold brewed beverage is provided. The system of the present invention includes automatically controllable integrated components for purifying the water supplied to brew the beverage and for maintaining the system in a sanitary condition that can be serviced on site or from a remote location. The present invention further provides an automated, commercial scale method for brewing tea from real tea leaves and naturally sweetening the tea to produce cold sweet tea with the high quality taste of homemade sweet tea.

Further objects and advantages will be apparent from the following description, drawings, and claims.

DESCRIPTION OF THE INVENTION

Iced tea, particularly sweetened iced tea, has become more popular in recent years and is increasingly requested by patrons in a wide range of restaurants in place of carbonated soft drinks. The vast majority of fast food outlets and many other restaurants have met customer demands with tea products required to be purchased with the carbonated soft drinks offered by their beverage supplier. These tea products are typically produced as a concentrate from ground tea or tea sweepings, are flavored and sweetened with artificial flavorings and sweeteners, and are packaged to be dispensed with the carbonated beverages. Such tea beverages often have an "off" taste and, as a result, generate little repeat business. Some restaurants do brew their own tea, and the quality varies widely from batch to batch. Brewed tea has a short storage life and can deteriorate rapidly, which affects the quality of the taste. Many iced tea drinkers prefer presweetened iced tea, which presents additional challenges to restaurants that brew tea and add sweetener. At ambient temperatures, moreover, undesirable microbial growth that affects the taste of the tea can occur.

The present invention is an improvement of the iced tea brewing and dispensing systems shown and described in Applicant's U.S. Pat. Nos. 4,919,041 and 5,116,632, the disclosures of which are hereby incorporated herein by reference. The system and method shown and described in the aforementioned patents produces a very high quality presweetened iced tea product that meets restaurant quantity requirements, but its effective operation has proved to be quite labor intensive. This is a disadvantage when trained workers are hard to find.

The cold brewed beverage brewing, sweetening, and dispensing system of the present invention overcomes the problems described above and provides an automatically controllable commercial scale system for brewing tea from fresh tea leaves and purified water, sweetening the tea, dispensing cooled sweetened tea with a high quality superior taste, and maintaining the system in a condition that produces consistently high quality, superior taste tea. The control system of the present invention is designed to be monitored and actuated for optimum maintenance and service on site as well as from remote service locations.

Figure 1:
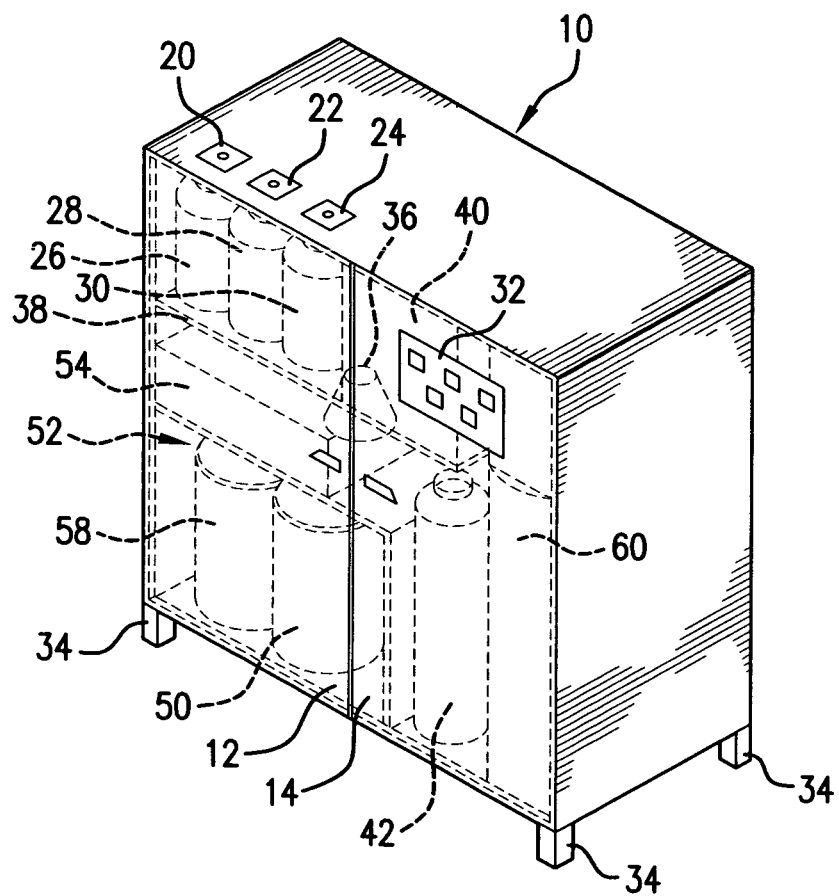
FIG. 1 is a front perspective diagrammatic view of the cold beverage brewing and dispensing system of the present invention.
Figure 3:
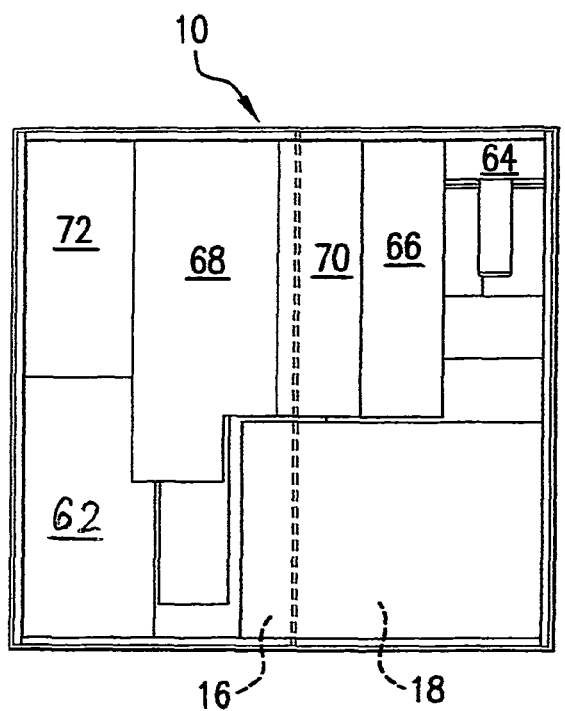
FIG. 3 is a back diagrammatic view of a preferred arrangement of the components of the cold beverage brewing and dispensing system of the present invention.

Referring to the drawings, FIG. 1 illustrates a front perspective diagrammatic view of a preferred embodiment of the tea brewing and dispensing system of the present invention. The present tea brewing and dispensing system has been designed to have a compact, space-saving configuration so that it will fit through a standard 30 inch door. The system components are mounted in a cabinet 10 that is preferably formed of a stainless steel material suitable for food service applications. The cabinet 10 is designed to allow access to the interior when necessary for service or maintenance, yet limit access to designated persons. A series of access doors that can be outfitted with programmable locks or other like devices are provided. Access doors 12,14 on the front of the cabinet 10 allow the components in the interior front of the cabinet to be reached. Movable access panels 16, 18, shown in FIG. 3, are designed to provide access to components in the back of the cabinet, and access doors 20, 22, and 24 on the upper surface of the cabinet allow filling of tea leaf reservoirs 26, 28, and 30. An exterior LCD type display panel 32 may be provided on one of the access doors 12, 14 or mounted in another convenient location on the exterior of the cabinet to provide information relating to the operation of the system, including, but not limited to the quantity of liquids in the various reservoirs, the phase of the operating cycle, and other system parameters. The cabinet 10 can be adapted to be mounted on casters (not shown) for portability or legs (34) in a permanent installation.

Figure 2:
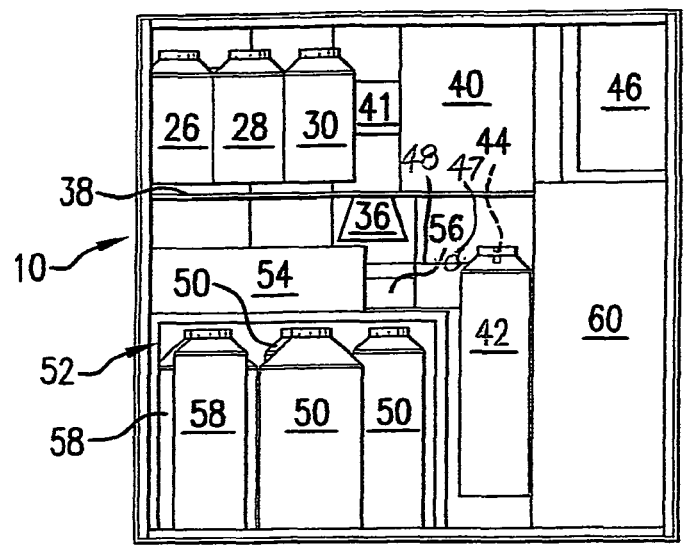
FIG. 2 is a front diagrammatic view of a preferred arrangement of the components of the cold beverage brewing and dispensing system of the present invention.

FIGS. 2 and 3 together illustrate diagrammatically the main components of the present tea brewing and dispensing system. Tea leaf reservoirs 26, 28, and 30 are mounted within the cabinet 10 under their respective access doors 20, 22, and 24. Stainless steel beverage cans in a 3 gallon size may be conveniently modified to form the tea leaf reservoirs 26, 28, and 30. One modification is the inclusion of a signal actuated door or the like (not shown), preferably in the base of each tea leaf reservoir, that can be programmed to release a predetermined amount of loose tea leaves into an infuser brew basket 36 when the brew basket is positioned beneath a tea leaf reservoir as will be described below. The infuser brew basket 36 is designed to be mounted on a track 38 so that the basket is movable into any one of five different positions and invertable to dispose of used tea leaves. Basket 36 is shown in its inverted position in the drawings. In positions one, two, and three, the basket 36 is aligned with one of the tea leaf reservoirs to receive a quantity of fresh tea leaves. In position 4, the basket 36 is aligned with an automatic tea brewing apparatus 40. The positioning and alignment of the basket 36 under the tea brewing apparatus includes a switch or like activator (not shown) programmed to activate the tea brewer 40 to turn the brewer on to start the tea brewing cycle and then to turn off the tea brewer at the end of the tea brewing cycle.

The automatic tea brewer 40 is preferably the type of automatic tea brewer that can be programmed to brew a desired quantity of tea within a selected time period. There are many available automatic tea brewers that have this capability. A preferred brewing type of tea brewer will brew about 5 gallons of tea in 15 minutes when activated by the infuser brew basket 36.

The brewed tea is collected in a tea receptor 42. The tea receptor is configured similarly to a 5 gallon beverage can of the type used in food service applications. The tea receptor includes an inlet valve 44 in fluid communication and aligned with the infuser brew basket 36 and the tea brewing apparatus 40. The inlet valve 44 is programmed to open when the tea brewing apparatus is activated to begin the tea brewing cycle by the positioning of the brew basket 36. At the end of the tea brewing cycle, the tea receptor inlet valve 44 is activated, causing it to close. An actuating signal is concurrently sent to an inlet port (not shown) located on the tea receiver, causing it to open to received compressed air from a pump 46 fluidically connected to the inlet port, thereby propelling tea through an outlet port (not shown) located in the tea receptor 42.

The tea is moved through the outlet port by the compressed air to a three way valve 47 that is selectively activated to direct pressurized tea through an appropriate fluid line 48 to a selected one of three pressurized tea reservoirs 50 located in a section 52 of the cabinet 10 that is refrigerated. One of a battery of circulating pumps and motors 54 is fluidically connected to a designated tea reservoir 50 to direct the brewed tea from that reservoir through a chiller coil (not shown) in a continuous circuit that includes a fluid connection with a conventional tea dispenser (not shown) of the type used by the food service industry to dispense chilled beverages and with a drain valve (not shown). Two other of the battery of circulating pumps and motors 54 are fluidically connected with each of the other two tea reservoirs 50 and circulate pressurized brewed tea from these tea reservoirs in a similar manner. If desired, the system can be set up to brew and dispense only one kind of tea or to brew and dispense three different kinds of tea, one kind of tea at a time. This would enable the restaurant to have available, for example, black tea, green tea, and herbal tea for its customers.

When the automatic tea brewer 40 has completed the brewing cycle, the infuser brew basket 36 is moved to a fifth position above a drain basin 56, where the basket containing wet tea leaves is activated to cause it to invert over the drain basin, thereby dumping the used tea leaves into the drain basin 56. A conventional spray device mounted with the drain basin is further activated to rinse the basket 36, which is preferably then air dried until activated to begin a new brew cycle. The track 38 on which the infuser brew basket 36 is mounted may be configured in any one of a number of ways known to those skilled in this art. One type of track suitable for this purpose resembles a bicycle chain mounted on sprockets.

A liquid sweetener, preferably one based on cane sugar as described in Applicant's U.S. Pat. Nos. 4,919,041 and 5,116,632, is premixed and placed in sweetener reservoirs 58 in the refrigerator section 52 of the cabinet 10. The sweetener reservoirs 58 are fluidically connected to a dedicated sweetener pump in the battery of pumps and motors 54, which continuously circulates sweetener in a continuous circuit that includes a chiller coil so that the sweetener is maintained in a chilled condition. The chiller fluid circuit is fluidically connected with the dispenser (not shown) that dispenses the chilled brewed tea. When sweetened tea is to be dispensed, both a selected tea circuit and the sweetener circuit are activated simultaneously to dispense both cold tea and cold sweetener concurrently. If unsweetened tea is desired, only a selected tea circuit is activated to dispense cold unsweetened tea.

Although the entire fluid circuit is not shown in detail in the drawings, the components of the tea brewing and dispensing system of the present invention are in fluid communication as described and include fluid lines and connections as needed to circulate and dispense the treated water, brewed tea, and sweetener required to produce a superior brewed tea product.

The fluid lines contemplated for use in the present invention are of the type conventionally used in food service applications, such as, for example, hoses made of flexible synthetic materials.

Other components mounted in the cabinet 10 that are part of the automatic tea brewing and dispensing system of the present invention include a water storage tank 60 for storing water that has been purified to produce brewed tea with a high quality taste. A space 62 to house a condenser (not shown) for the refrigerated section 52 is also located in the cabinet 10. In addition, an air treatment system 72 is preferably included in the cabinet 10 to filter, dry and compress ambient air for use in the tea, sweetener, and sanitizing circuits. A climate control component 41 (FIG. 2) should also be installed in the cabinet 10 to protect the electronic components from overheating. The foregoing components are available commercially.

FIG. 3 illustrates additional components of the tea brewing and dispensing system of the present invention. The consistently superior tasting tea produced by this system results in large part from the treatment and purification of the water used to make the tea and sweetener. Water enters the cabinet through fluid lines (not shown) connected to a supply of water. Typically the water will come from a municipal water supply. Water entering the cabinet first flows through an automatic sediment filter 64 to remove any solids and then through an ultraviolet disinfectant system 66 to eliminate some of the contaminants that could be present in the water. A reverse osmosis type of water purification system 68, preferably one capable of purifying 800 gallons per day, treats the water further before it is directed to the automatic tea brewer.

Additional water used by the tea brewing and dispensing system of the present invention is treated by an ozonator 70 that makes ozonated water from ambient air and water. Ozonated water is a very powerful disinfectant that is significantly more effective than chlorine and has been approved for food contact by the Food and Drug Administration (FDA). Ozonated water has been demonstrated to effectively eliminate bacteria such as *E. coli* and *Salmonella*, as well as other bacteria and viruses. To produce commercially effective amounts of ozonated water, ozone must be produced on site. The present invention is designed to generate sufficient ozone to accomplish this result. The ozonated water produced in conjunction with the tea brewing and dispensing system of the present invention can be used to sanitize the system as described below and will also be available in sufficient quantity for such other uses as sanitizing hands and rinsing food.

Figure 4:
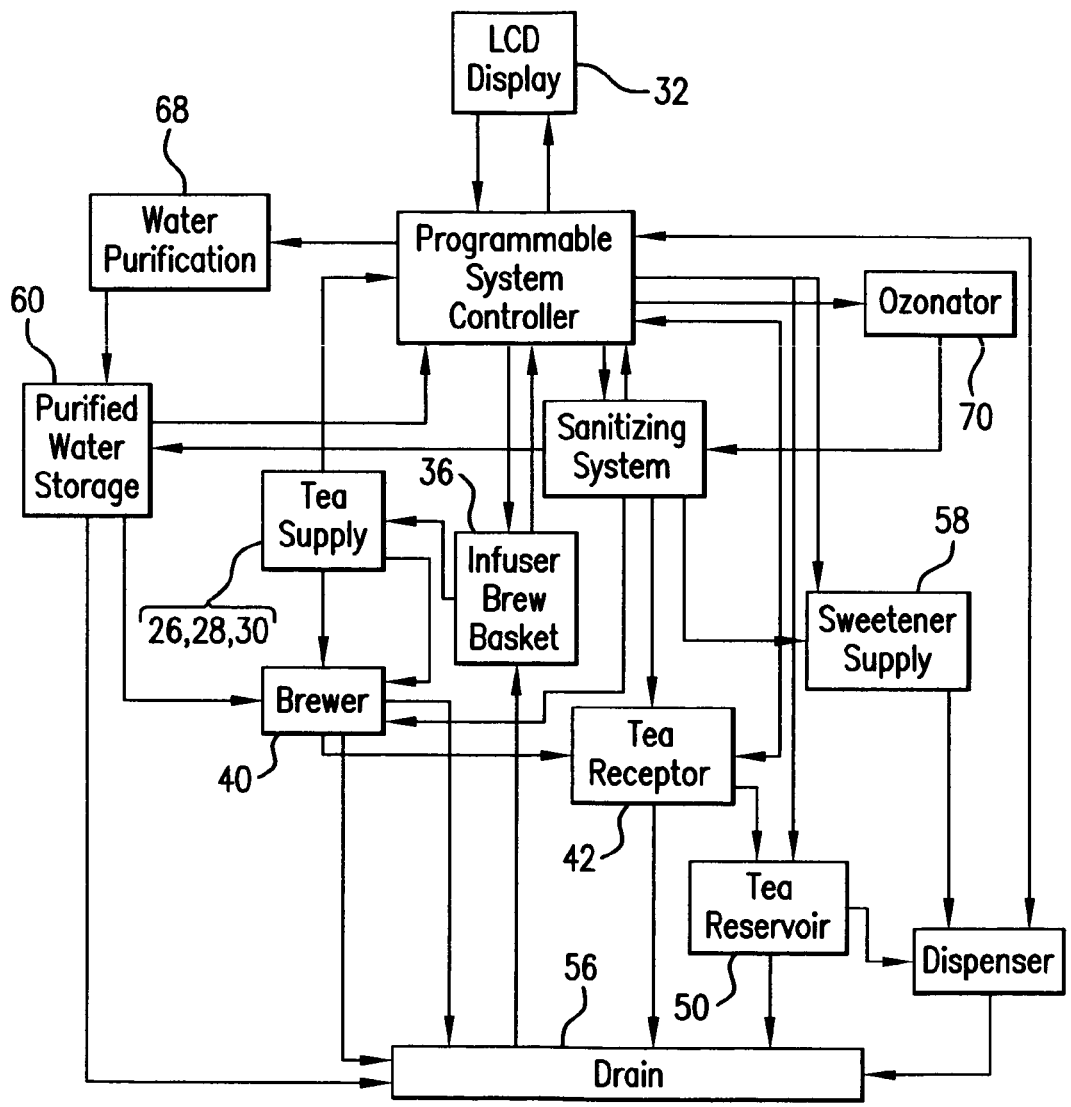
FIG. 4 is a flow chart showing operation of the components of the cold beverage brewing and dispensing system of the present invention.

The operation of the tea brewing and dispensing system of the present invention is designed to be substantially completely automatic. FIG. 4 illustrates one possible automated embodiment of the present invention. Once an installer or operator has set the parameters of the system, it can be fully automated. When a brewing and dispensing system has been installed, a restaurant then selects the time of day it wishes to begin serving brewed iced tea and the time of day it wants the system set to stand by. Sanitization of the system requires a two hour time period. For example, if the system is set for sanitizing at 2:00 AM, and start up is set for 4:00 AM, the LCD display panel 32 on the cabinet will display Stand By, Start Up, Ready, and Sanitizing. The LCD will also display the amount of product in the tea leaf reservoirs 26, 28, and 30 and sweetener reservoirs 58. When the system starts to operate, the LCD will change from Stand By to Start Up, indicating that the system is turned on. A signal from a system processor activates the infuser brew basket 36 to revert to an upright position and moves basket 36 along track 38 to a first position in communication with tea leaf reservoir 26. Tea leaf reservoir 26 is activated to release a predetermined quantity of tea leaves sufficient to make 5 gallons of brewed tea, and the basket 36 is activated to move to a second position in communication with the automatic tea brewer 40. This initiates the brew cycle and signals the tea receiver inlet valve 44 to open so that the tea receiver can collect the brewed tea. At the end of the 15 minute brewing cycle, the inlet valve 44 closes, and system signals activate the components required to move the brewed tea from the tea receiver to a tea reservoir 50 in the refrigerator part of the cabinet.

When the system is in Ready mode, sensors are activated to detect tea reservoir levels. If the levels are lower than a selected minimum volume, the basket 36 is signaled to begin a new brew cycle.

At a preset time, the LCD will change from Ready to Sanitize, and all tea reservoirs and fluid circuits will be automatically emptied. Ozonated water will be directed to the tea receiver 42; from there the ozonated water will be pressurized and circulated through all of the tea circuits. The drain valve (not shown) is activated to open and close as needed.

The operation of the tea brewing and dispensing system of the present invention has been described with respect to activators, actuators, signals, and processors. Most of these electronic components are known in the art. The present tea brewing system is intended to be capable of automatic operation, and employs suitable arrangements of these electronic components to achieve the automatic brewing of both sweetened and unsweetened tea and the sanitizing of the components of the system. It is contemplated that wireless technology will be employed in conjunction with electronic processors and microprocessors to enable control of the present system from a remote location as well as at the site where the system is installed.

Although the tea brewing and dispensing system of the present invention has been described with respect to preferred embodiments, structures and components that are functionally equivalent to those described herein are intended to fall within the scope of the present invention.

Industrial Applicability

The tea brewing and dispensing system of the present invention will be used primarily in the food service industry, such as in fast food outlets and other restaurants. The present tea brewing and dispensing system will also find use in other venues where the commercial scale production of a consistently high quality brewed sweetened or unsweetened tea is desired, including educational institutions, hospitals, and other similar users of commercial food service equipment.

The invention claimed is:

1. A system for controllably and automatically producing on a commercial scale a high quality cold tea beverage that can be dispensed in a sweetened or in an unsweetened condition, comprising, substantially completely contained within a controlled access cabinet means:
 a. a tea brewing system component configured to automatically and controllably brew a high quality tea beverage directly from a controlled supply of fresh tea leaves and purified water and to hold and maintain the high quality tea beverage in a cold condition until dispensed, and comprising a plurality of tea leaf reservoirs comprising containers, wherein a first end of each said container is designed to register with a corresponding access means in said cabinet means to receive a supply of fresh tea leaves and a second, opposed end of each said container is configured to dispense automatically a selected quantity of fresh tea leaves; and a brew basket mounted to be automatically movable from a position to receive an automatically dispensed selected quantity of fresh tea leaves from a second end of a tea leaf reservoir to a position aligned with an automatic tea brewing means to brew automatically said high quality tea beverage with water from said water purification system component and then to an inverted position wherein used tea leaves are dumped after brewing
 b. a sweetener system component fluidically integral with said tea brewing system and configured to hold and maintain a supply of a liquid sweetener comprising naturally occurring sweeteners in a cold condition;
 c. a water purification system component and a sanitizing system component, each said component being fluidically integral with said tea brewing system component and said sweetener system component, wherein said water purification system component comprises filter means, disinfecting means, and reverse osmosis purification means designed to provide a supply of purified water to said tea brewing system component to brew said high quality tea beverage, and wherein said sanitizing system component comprises ozone generation means to produce ozonated water from said purified water and means for automatically directing ozonated water through said tea brewing system component and said sweetener system component to sanitize said tea brewing system component and said sweetener system component when said system is not automatically and controllably producing or dispensing said high quality cold tea beverage; and
 d. a programmable system controller designed to be programmed to automatically control and operate said system components whereby said high quality cold tea beverage is consistently produced on a commercial scale.

2. The system of claim 1, wherein said tea brewing system component comprises:
 a. a tea receptor fluidically connected to said automatic tea brewing means to receive and temporarily hold the brewed high quality tea beverage; and
 b. one or more tea reservoirs fluidically connected to said tea receptor and to a source of pressurized gas whereby the brewed high quality tea beverage is moved from the tea receptor to a tea reservoir, wherein said one or more tea reservoirs and said supply of sweetener are positioned within a chiller portion of said cabinet means to maintain said brewed tea and said sweetener in a cold condition at an optimum temperature.

3. The system of claim 1, further comprising dispenser means located outside said cabinet means and fluidically connected to said tea brewing system component and said sweetener system component configured to selectively deliver automatically a desired quantity of cold brewed high quality cold tea beverage from said tea brewing system component or a predetermined quantity of cold sweetener from said sweetener system component concurrently with a desired quantity of said brewed high quality tea beverage.

4. The system of claim 3, further comprising fluid connection and actuation means for fluidically and controllably connecting said tea brewing system component, said water purification system component, said sweetener system component, said sanitizing system component, and said dispenser means to automatically move loose tea leaves, brew tea with purified water, dispense cold brewed tea, dispense cold brewed tea and sweetener, and move ozonated water through said system.

5. The system of claim 4, further comprising actuation and control means programmable to activate and control activation of said tea brewing system component, said sweetener system component, said water purification system component, and said sanitizing system component to consistently produce a high quality cold unsweetened or sweetened tea beverage.

6. The system of claim 5, wherein said controlled access cabinet, means is configured to mount and hold in compact functional arrangement at least said tea brewing system component, said sweetener system component, said water purification system component, said sanitizing system component, said fluid connection and actuation means, and said actuation and control means.

7. The system of claim 2, further comprising a track supporting and automatically controlling movement of said brew basket from engagement in a receive position with a selected tea leaf reservoir to receive loose tea leaves to a brew position in alignment with said automatic tea brewing means to provide said loose tea leaves for use in brewing said high quality tea beverage, wherein said track is automatically actuatable to move the brew basket from said receive position to said brew position to said inverted position to dump the tea leaves after said high quality tea beverage has been brewed, and then back to a receive position.

8. The system of claim 1, further comprising drain means located within said cabinet means to receive used tea leaves, brewed tea, sweetener, or water to be discarded and ozonated water used to sanitize said system.

9. The system of claim 1, wherein said water purification system components means filter means comprises an automatic sediment filter and said disinfecting means comprises an ultraviolet disinfectant system.

10. The system described in claim 2, wherein the brew basket comprises a water permeable receptacle configured to activatably engage said tea leaf reservoir to dispense a predetermined quantity of loose tea leaves and then to activatably engage said automatic tea brewing means after the loose tea leaves have been dispensed into the receptacle.

11. The system described in claim 2, wherein said tea receptor includes actuatable valve means programmable to open or close in response to the position of said brew basket in fluid contact with said automatic tea brewing means.

12. The system described in claim 11, wherein said tea receptor further comprises selectively actuatable three way valve means for providing a separate fluid connection with each of three tea reservoirs, wherein said actuatable three way valve means may be actuated to direct high quality brewed tea to a selected tea reservoir.

13. The system described in claim 4, further including system pressurizing means for moving purified or ozonated water, brewed iced tea, and sweetener through said system.

14. The system described in claim 1, wherein said sanitizing system component is configured to direct said ozonated water through the system in response to a programmable timed signal.

15. The system described in claim 5, wherein said controlled access cabinet means includes display panel means connected to said actuation and control means for communicating information relating to the operation and status of the brewing and dispensing system.

16. The system described in claim 3, wherein said dispenser means includes a fluid connection with a selected tea reservoir and a fluid connection with said sweetener system component, and said dispenser is programmable and actuatable to activate one or both of said fluid connections to selectively dispense either unsweetened tea or sweetened tea.

17. The system described in claim 2, wherein said system further comprises drain means for directing used tea leaves, tea, sweetener, and sanitizing fluids out of the system.

18. The system described in claim 2, wherein said plurality of tea leaf reservoirs comprises three separate containers and each of said containers holds a different variety of tea.

* * * * *